United States Patent
Aymard et al.

(10) Patent No.: US 9,994,874 B2
(45) Date of Patent: Jun. 12, 2018

(54) METHOD FOR PRODUCING ALCOHOLS AND/OR SOLVENTS FROM A BIOMASS, INCLUDING RECIRCULATING AN INTERNAL FLOW INCLUDING ALCOHOLS AND/OR SOLVENTS UPSTREAM FROM OR WITHIN THE PRETREATMENT

(71) Applicant: IFP Energies nouvelles, Rueil-Malmaison (FR)

(72) Inventors: Caroline Aymard, Lyons (FR); Marcel Ropars, Palaiseau (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days. days.

(21) Appl. No.: 14/436,791

(22) PCT Filed: Sep. 25, 2013

(86) PCT No.: PCT/FR2013/052260
§ 371 (c)(1),
(2) Date: Apr. 17, 2015

(87) PCT Pub. No.: WO2014/060673
PCT Pub. Date: Apr. 24, 2014

(65) Prior Publication Data
US 2015/0240268 A1  Aug. 27, 2015

(30) Foreign Application Priority Data
Oct. 18, 2012  (FR) .................................. 12 02806

(51) Int. Cl.
*C12P 7/16* (2006.01)
*C12P 7/04* (2006.01)
*C12P 7/10* (2006.01)
*C12P 7/14* (2006.01)

(52) U.S. Cl.
CPC ...... *C12P 7/16* (2013.01); *C12P 7/04* (2013.01); *C12P 7/10* (2013.01); *C12P 7/14* (2013.01); C12P 2201/00 (2013.01); C12P 2203/00 (2013.01); Y02E 50/10 (2013.01); Y02E 50/16 (2013.01)

(58) Field of Classification Search
CPC ................... C12P 7/14; Y02E 50/16
See application file for complete search history.

(56) References Cited

U.S. PATENT DOCUMENTS

| | | | |
|---|---|---|---|
| 7,465,791 B1 | 12/2008 | Hallberg et al. | |
| 7,649,086 B2 | 1/2010 | Belanger et al. | |
| 7,985,847 B2 | 7/2011 | Belanger et al. | |
| 8,528,463 B2 | 9/2013 | Hallberg et al. | |
| 8,822,657 B2 | 9/2014 | Belanger et al. | |
| 2002/0006998 A1 | 6/2002 | Pye et al. | |
| 2007/0259412 A1 | 11/2007 | Belanger et al. | |
| 2008/0299629 A1 | 12/2008 | Hallberg et al. | |
| 2010/0136642 A1* | 6/2010 | Belanger ................ | D21C 5/00 435/161 |
| 2011/0282038 A1 | 11/2011 | Belanger et al. | |
| 2012/0100585 A1* | 4/2012 | Ropars ..................... | C12P 7/10 435/150 |
| 2012/0289685 A1 | 11/2012 | Hallberg et al. | |
| 2013/0005952 A1 | 1/2013 | Belanger et al. | |

FOREIGN PATENT DOCUMENTS

| | | |
|---|---|---|
| CN | 101942482 A | 1/2011 |
| CN | 101942483 A | 1/2011 |
| WO | 2007129921 A1 | 11/2007 |

OTHER PUBLICATIONS

International Search Report for PCT/FR2013/052260 dated Mar. 3, 2014.
Hii, K. et al, "Pretreatment of Pressed Pericarp Fibers (PPF) Using Alcohols as Solvent to Increase the Accessibility of Cellulose for Cellulase Production," J. Korean Soc Appl Biol Chem, 2012, vol. 55, pp. 507-514
Rughani, J. et al., "Combined Rapid-Steam Hydrolysis and Organosolv Pretreatment of Mixed Southern Hardwoods," Biotechnology and Bioengineering, 1989, vol. 33, pp. 681-686.
Hongzhang, C. et al., "Unpolluted fractionation of wheat straw by steam explosion and ethanol extraction," Bioresource Technology, 2007, vol. 98, pp. 666-676.
Dutta, A. et al., "An Economic Comparison of Different Fermentation Configurations to Convert Corn Stover to Ethanol Using *Z. mobilis* and *Saccharomyces*," Biotechnol. Prog., 2010, vol. 26, No. 1, pp. 64-72.
Zhao, X. et al, "Organsolv pretreatment of lignocellulosic biomass for enzymatic hydrolysis," Appl Microbiol Biotechnol, 2009, vol. 82, pp. 815-827.
Ahn, J. et al., "Butanol production from thin stillage using Clostridium pasteurianum," Bioresource Technology, 2011, vol. 102, pp. 4934-4937.
Green, E. M. et al., "Fermentative production of butanol—the industrial perspective," Current Opinion in Biotechnology, 2011, vol. 22, pp. 337-343.
English Abstract of CN101942483, Publication Date: Jan. 12, 2011.
English Abstract of CN101942482, Publication Date: Jan. 12, 2011.

* cited by examiner

*Primary Examiner* — Louise W Humphrey
*Assistant Examiner* — Stephen A Perkins
(74) *Attorney, Agent, or Firm* — Millen, White, Zelano and Branigan, P.C.

(57) ABSTRACT

The invention relates to a process for the production of alcohols from biomass that comprises a stage in which at least one aqueous internal flow that comprises at least one alcohol that has n carbon atoms, with n between 2 and 5, is recycled, provided that when the alcohol comprises 2 carbon atoms, it is mixed with at least one other alcohol in such a way as to recover a vapor phase effluent that contains alcohols exiting from said pretreatment reactor.

15 Claims, 6 Drawing Sheets

METHOD FOR PRODUCING ALCOHOLS AND/OR SOLVENTS FROM A BIOMASS, INCLUDING RECIRCULATING AN INTERNAL FLOW INCLUDING ALCOHOLS AND/OR SOLVENTS UPSTREAM FROM OR WITHIN THE PRETREATMENT

FIELD OF THE INVENTION

This invention is part of the framework of a process for the production of so-called "second generation" alcohols from lignocellulosic biomass.

PRIOR ART

The lignocellulosic biomass represents one of the most abundant renewable resources on earth. The substrates considered are very varied, since they relate both to the ligneous substrates (leafy and resinous), the by-products of agriculture (straw), or those of the lignocellulosic waste-generating industries (farm produce and papermaking industries).

The lignocellulosic biomass consists of three main polymers: cellulose (35 to 50%), hemicellulose (20 to 30%), which is a polysaccharide that consists essentially of pentoses and hexoses, and lignin (15 to 25%), which is a polymer of complex structure and high molecular weight, consisting of aromatic alcohols that are connected by ether bonds.

These different molecules are responsible for the inherent properties of the vegetation wall and are organized in a complex intertwining.

Cellulose and optionally hemicelluloses are the targets of enzymatic hydrolysis but are not directly accessible to the enzymes. This is the reason for which these substrates are to undergo a pretreatment preceding the enzymatic hydrolysis stage. The purpose of the pretreatment is to modify the physical and physico-chemical properties of the lignocellulosic material for the purpose of improving the accessibility of the cellulose that is imprisoned within the matrix of lignin and hemicellulose.

Numerous technologies for carrying out this pretreatment exist. It is possible to cite, for example, acid baking, alkaline baking, vapor explosion, Organosolv processes, etc.

The effectiveness of pretreatment is measured both by the material balance at the end of the pretreatment (recovery rate of sugars in the form of soluble monomers or oligomers or insoluble polymers) and also by the cellulosic and hemicellulosic residues' susceptibility to enzymatic hydrolysis.

The pretreatment by vapor explosion is distinguished by its performances in terms of degradability of cellulose and its low dilution rate.

The pretreatment by vapor explosion is also known by the name "steam explosion," "steam gunning," "explosive pressure relief," and "pretreatment with vapor." The plant is brought quickly to high temperature (150°-250° C.) by injection of pressurized vapor. Treatment is stopped in general by sudden decompression, called pressure relief or explosion, which destructures the lignocellulosic matrix. The dwell times vary from 10 seconds to several minutes for pressures ranging from 10 to 50 bar. This technique has been used either intermittently or continuously. Certain technologies propose an injection of water for cooling the medium before the decompression.

Numerous configurations are possible for this type of pretreatment. The implementation may be of the batch type or of the continuous type. The vapor explosion may be preceded by an impregnation of acid for promoting the hydrolysis of hemicelluloses during the baking. When the vapor explosion is applied on a substrate that is previously acidified, for example with $H_2SO_4$, it leads to a solubilization and an almost-total hydrolysis of hemicelluloses into their monomers by limiting the degradation into furfural. In addition, the susceptibility of cellulose to enzymatic hydrolysis is improved. The use of an acid catalyst makes it possible to reduce the temperature of the process (150 to 200° C. versus 250° C. for the vapor explosion without a catalyst) and thus to minimize the formation of degradation compounds.

The vapor explosion may be preceded by an acid baking stage whose purpose is to hydrolyze the hemicelluloses and to remove them in a liquid solution in the form of monomeric sugars and/or oligomers.

The significant parameters are in particular temperature, duration, and the presence of acid (type and concentration). These parameters act together on the reactivity of the substrate to enzymatic hydrolysis, and their effects are interchangeable to a certain extent. Thus, for example, a longer duration can compensate for a lower temperature.

The biochemical processes for the production of alcohols from lignocellulosic biomass, called "second-generation processes," comprise at least the following stages:
 Pretreatment of the substrate,
 Enzymatic hydrolysis of the pretreated substrate,
 Fermentation into alcohols of the hydrolyzate that is obtained, and
 Separation/purification of the alcohols that are obtained after fermentation.

The economic validity of this type of process for the production of alcohols is difficult to achieve even for the operators that have broad mobilizable resources. Several items have a strong impact on the overall operating cost of the units; it is possible to cite in particular the cost of the plant resources and the energy used in the stages for separation and purification of the alcohols that are most often produced by distillation. The optimization of this type of process requires optimum upgrading of all of the sugars as well as appropriate management of the thermal integration of the process.

PARTICULAR DEFINITIONS

In terms of this invention, the soluble monomers and oligomers of sugars that comprise 5 carbon atoms are referred to as "pentoses," and the soluble monomers and oligomers of sugars that comprise 6 carbon atoms are referred to as "hexoses."

The dry materials (solid and soluble) that are present in a medium are referred to by the abbreviation "MS," and the materials in suspension (solids) that are present in a medium are referred to by the abbreviation "MES." The level of dry materials (or "total solids") is determined according to the method that is described by ASTM E1756-01, which consists of a loss of mass at 105° C.

The conversion by biological means of sugars into one or more alcohols and optionally into a mixture with ketones is referred to by the term "alcoholic fermentation." The alcoholic fermentation according to the invention can be conducted under anaerobiosis or aerobiosis in the presence of "wild" or "genetically modified" microorganisms.

This term includes in particular:
A) Ethylic fermentation that corresponds to the production of ethanol by itself by means of yeasts (for example, *S. cerevisiae*) or bacteria (for example, *Z. mobilis*) or other microorganisms.

B) "Butylic" fermentation, which itself combines here:

A fermentation producing n-butanol alone;

An "ABE" fermentation that corresponds to the production of a mixture that comprises acetone, n-butanol (majority product), ethanol. Traces of isopropanol can also be present.

An "IBE" fermentation that corresponds to the production of isopropanol, n-butanol (majority product), and ethanol.

These types of fermentation are in general carried out by means of microorganisms of the genus *Clostridium* and are conducted under strict anaerobiosis:

An "isobutylic" fermentation that in general corresponds to the production of isobutanol alone. Numerous microorganisms, all genetically modified, are able to carry out this conversion (for example, *E. coli, Corynebacterium, S. cerevisiae*) from the path of amino acids.

C) The "propylic" fermentation, which corresponds to the production of propanol or isopropanol.

In summary, the term "alcoholic fermentation" within the meaning of this invention comprises the ethylic, butylic, and isobutylic types of fermentation, but also other types of fermentation making possible the production of other alcohols.

SUMMARY OF THE INVENTION

One object of the invention is therefore to propose a process for the production of alcohols that have two or more carbon atoms from biomass and for which the balances of energy and water are optimized.

The process according to the invention comprises at least the following stages:
a) In a pretreatment reactor, the biomass is pretreated by vapor explosion in such a way as to produce an effluent that contains a pretreated substrate;
b) Enzymatic hydrolysis of the pretreated substrate contained in the effluent obtained from stage a) is carried out in the presence of cellulolytic and/or hemicellulolytic enzymes in such a way as to produce a hydrolyzate that contains solubilized sugars;
c) Alcoholic fermentation of the solubilized sugars contained in the hydrolyzate obtained from stage b) is carried out in alcohols that have two or more carbon atoms, in the presence of an alcohologenic microorganism in such a way as to produce a fermented effluent;
d) A stage for extraction of alcohols that have two or more carbon atoms of the fermented effluent obtained from stage c) is carried out, and a stage e) in which there is recycled—upstream from or in the pretreatment reactor—at least one aqueous internal flow that comprises at least one alcohol that has n carbon atoms, with n between 2 and 5, provided that when the alcohol comprises n=2 carbon atoms, it is in a mixture with at least one other alcohol, in such a way as to recover a vapor phase effluent that contains alcohols exiting from said pretreatment reactor.

The invention thus exploits the property of the $C_2$ and $C_3$ alcohols of being more volatile than water and the property of $C_4$ and $C_5$ alcohols of forming an azeotrope with water—and therefore the boiling point is lower than that of water—and thus promotes the distribution of these alcohols in the vapor phase during the pressure relief. The alcohols that are then sent to the extraction stage are already in vapor form, which makes it possible to reduce the energy cost of the separation by distillation and therefore the overall energy cost of the process. The other portion of the alcohols that is not recovered in the vapor phase is found in the liquid effluent that is extracted from the pretreatment reactor and contributes to increasing the titer of the wine or wines that are extracted from the main fermentation reactor.

In addition, the recycled internal flow can advantageously and easily be integrated thermally into the overall scheme of the process according to the invention. Thus, before being recycled, the internal flow can be heated in advance by means of a hot flow produced during the extraction stage that generally implements at least one distillation stage.

Furthermore, the recycling of an aqueous flow makes it possible to reuse a portion of the water in the pretreatment stage by vapor explosion and therefore goes in the direction of an optimization of the water balance of the process.

The process makes it possible to produce primarily alcohols that preferably have 2, 3, 4 or 5 carbon atoms, by themselves or in a mixture. It is possible to cite, for example, ethanol by itself, ethanol in a mixture with n-butanol, ethanol in a mixture with isobutanol, propanol by itself or in a mixture, isopropanol by itself or in a mixture, isobutanol by itself or in a mixture, n-butanol by itself or in a mixture, or optionally a mixture of the ABE type or a mixture of the IBE type.

According to a preferred embodiment, the internal flow that is recycled comprises alcohols that are selected from among ethanol, propanol, isopropanol, butanol, by themselves or in a mixture, and provided that when the internal flow comprises ethanol, it is in a mixture with at least one alcohol that has 3 or 4 or 5 carbon atoms. Thus, the flow that is recycled upstream from or in the pretreatment reactor can comprise, for example, ethanol in a mixture with n-butanol, ethanol in a mixture with isobutanol, propanol by itself or in a mixture, isopropanol by itself or in a mixture, isobutanol by itself or in a mixture, n-butanol by itself or in a mixture, or optionally a mixture of the ABE type (acetone, n-butanol, ethanol) or a mixture of the IBE type (isobutanol, n-butanol, ethanol).

According to an embodiment, the process also comprises the following stages:
A solid/liquid separation of at least a portion of a vinasse produced in stage d) is carried out in such a way as to recover a liquid fraction that contains pentoses, and
A fermentation of the pentoses of the liquid fraction is carried out in such a way as to produce said internal flow that comprises alcohols.

According to another embodiment, the process also comprises the following stages:
A solid/liquid separation of at least a portion of the effluent that is obtained from stage a) is carried out in such a way as to recover a liquid fraction that contains solubilized sugars, and
A fermentation of the solubilized sugars of the liquid fraction is carried out in such a way as to produce said internal flow that comprises alcohols.

According to another embodiment of the process according to the invention, the process also comprises the following stages:
A solid/liquid separation of at least a portion of the effluent obtained in stage a) is carried out in such a way as to recover a pulp;
A washing of said pulp is carried out in such a way as to recover a liquid fraction that contains solubilized sugars;
Fermentation of solubilized sugars contained in the liquid fraction is carried out in such a way as to produce said internal flow that comprises alcohols.

According to another embodiment of the process according to the invention, the internal flow that contains alcohols is obtained from at least a portion of the fermented effluent produced in stage c).

According to an embodiment of the process according to the invention, the internal flow that contains alcohols is a liquid fraction that is obtained after solid/liquid separation of at least a portion of the fermented effluent produced in stage c).

According to an embodiment of the process according to the invention, the internal flow that contains alcohols is a liquid fraction that is obtained after washing a cake obtained by solid/liquid separation of at least a portion of the fermented effluent obtained in stage c).

According to another embodiment of the process according to the invention, the process also comprises the following stages:
 A solid/liquid separation of at least a portion of the hydrolyzate obtained in stage b) is carried out in such a way as to recover a pulp that contains hexoses and optionally pentoses, and
 A fermentation of the hexoses and optionally the pentoses contained in the pulp is carried out in such a way as to produce said internal flow that comprises alcohols.

According to another embodiment of the process according to the invention, the internal flow that contains alcohols is obtained from a stage for fermentation of a liquid fraction obtained after a stage for solid/liquid separation of at least a portion of the hydrolyzate obtained in stage b).

According to another embodiment of the process according to the invention, the stages b) and c) are carried out in the same reactor.

According to another preferred embodiment, the internal flow that contains alcohols is evaporated before the recycling stage e).

According to the invention, the cellulolytic and/or hemicellulolytic enzymes used during the hydrolysis stage can be produced by a microorganism that belongs to the genera *Trichoderma, Aspergillus, Penicillium* or *Schizophyllum*, or an anaerobic bacterium that belongs to the genus *Clostridium*.

According to the invention, the alcohologenic microorganisms used in the conversion unit for carrying out the fermentation of hexoses into alcohols are preferably selected from among the yeasts and the bacteria, optionally genetically modified. Preferably, microorganisms that are responsible for fermentation of the types ethyl, butyl (ABE, IBE, ABEI), and isobutyl are used.

The microorganisms that are used for the butylic fermentation stage are in general selected from among the strains that belong to the genus *Clostridium* (wild or genetically modified strains). These microorganisms are strictly anaerobic and capable of metabolizing the hexoses and the pentoses into butyl wine (ABE or IBE). They are also capable of converting certain oligomers effectively. Fermentation is generally carried out in batch mode, fed-batch, and, in a more advantageous way, continuously. The temperature is between 30 and 39° C., and the pH is between 4 and 7. The microorganisms are preferably selected from among the species *Clostridium beijerinckii, Clostridium saccharobutylicum, Clostridium saccharoperbutylacetonicum* and *Clostridium acetobutylicum*. All of these microorganisms are able to produce a mixture of acetone/butanol/ethanol or an ABE mixture, or an IBE mixture if isopropanol replaces the acetone.

For the isobutylic fermentation, it is possible to use genetically modified microorganisms such as those described by Atsumi et al. (Non-Fermentative Pathways for Synthesis of Branched-Chain Higher Alcohols as Biofuels. Nature, Vol. 451, Jan. 3, 2008) or by Baez et al. (High-Flux Isobutanol Production Using Engineered *Escherichia coli*: A Bioreactor Study with In Situ Product Removal. Appl Microbiol Biotechnol 90:1681-1690).

To carry out an ethylic fermentation, a yeast or a bacterium is selected. If a yeast is used, *Saccharomyces cerevisiae* is the one that is preferred. It is also possible to select yeasts such as *Schizosaccharomyces pombe* or *Saccharomyces uvarum* or *diastaticus*. More thermophilic yeasts, such as *Kluyveromyces fragilis* (now often referred to as *K. marxianus*), also exhibit an advantage, in particular when the enzymatic hydrolysis and the ethylic fermentation are carried out simultaneously (SSF process). A genetically modified organism, such as, for example, a yeast of the type *Saccharomyces cerevisiae* TMB 3400 (Ohgren et al., J. of Biotech 126, 488-498, 2006), can also be used. This yeast makes it possible in particular to ferment in ethanol a portion of the pentoses during the stage of ethylic fermentation of hexoses when the glucose is at a limiting concentration. When the microorganism is a bacterium, *Zymomonas mobilis* that has an effective assimilation path will be preferred. Just as for the yeasts, species of *Zymomonas mobilis* have been modified for converting the pentoses into ethanol in the same way as, for example, the strain *Zymomonas mobilis* 8b described by Dutta et al. (Biotechnol. Prog., 2010, Vol. 26, No. 1, pp. 64-72). The ethylic fermentation is preferably carried out at a temperature of between 30° C. and 40° C. and at a pH of between 3 and 6.5.

According to the invention, the microorganisms that are used for producing the internal flow that comprises alcohols from an internal flow that comprises sugars can preferably be selected from among the microorganisms that are responsible for the ethylic or butylic or isobutylic fermentation such as those described above.

Within the framework of this invention, it is possible to implement an extractive fermentation (also called fermentation with extraction) in which the fermentation reactor is completed by a device that is configured for extracting on line, in situ, in the presence of the microorganisms, at least a portion of the alcohols that are obtained from the main fermentation stage. The objective is to extract in a continuous way the alcohols that inhibit fermentation and that are produced so as to preserve a high yield. Thus, it is advantageous to use such a technique when the fermentation is of the butylic or isobutylic type (ABE, IBE) because they generate the butanol (n- and/or iso-) that is known for being a high-concentration fermentation inhibitor. The extraction techniques can be selected from among pervaporation, gas stripping, adsorption, perstraction, and liquid/liquid extraction. Within the framework of the invention, the internal flow that is recycled can thus be a secondary flow obtained from an extractive fermentation employing the technology of pervaporation, gas stripping or perstraction.

BRIEF DESCRIPTION OF DRAWINGS

These aspects as well as other characteristics and advantages of the invention will be clarified in the detailed description of particular embodiments of the invention, with reference being made to the drawings of the figures, in which.

In general, identical elements are indicated by the same references in the figures.

DETAILED DESCRIPTION OF THE INVENTION

Figure 1:
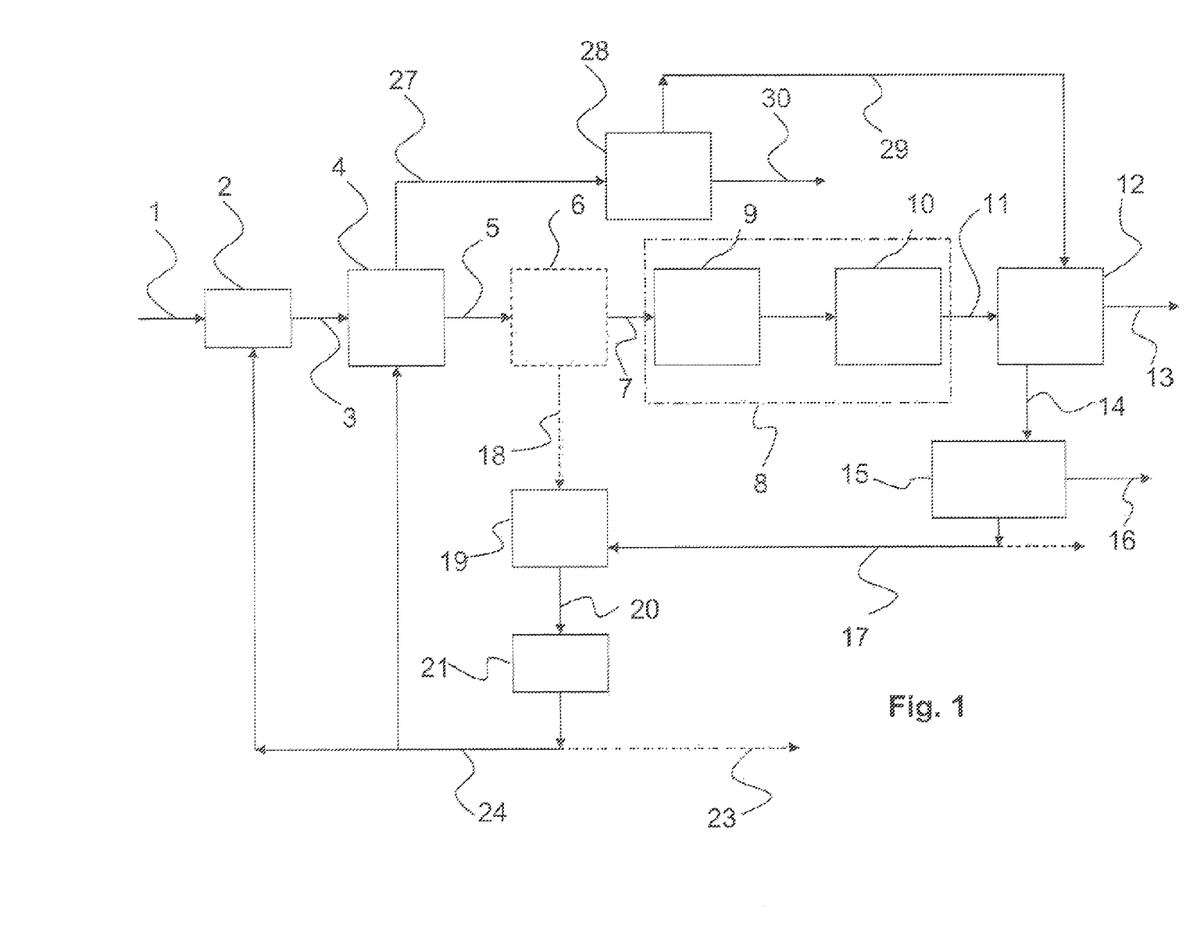
FIG. 1 is a diagrammatic representation of a first embodiment of the process for the production of alcohols according to the invention.

With reference to FIG. 1, the cellulosic and/or lignocellulosic substrate is introduced via the pipe 1 into a unit 2 for preparation of the feedstock. The water and/or the vapor necessary to the conduct of the feedstock preparation are introduced into the preparation unit by a dedicated line (not shown). The reagents (e.g., acid) and other utilities are introduced via another dedicated line (not shown). The feedstock preparation comprises, for example, a mechanical grinding, an addition of acid, an adjustment of the "MS" by adding water in liquid form and/or vapor form before the introduction into the vapor explosion reactor.

The cellulosic or lignocellulosic substrate that is used in the process according to this invention can be selected from among the most varied biomasses, but more particularly from the resinous arborescent species (softwood such as spruce or pine) or leafy arborescent species (hardwood such as eucalyptus) or agricultural lignocellulosic waste (corn straw, rice, etc.) or else dedicated crops (miscanthus, switchgrass).

The prepared substrate is introduced into the pretreatment reactor 4, via the line 3, which uses the vapor explosion technique. The vapor that is necessary to the pretreatment is introduced via a pipe (not shown). The vapor phase generated with pressure relief is extracted via the pipe 27.

The role of the pretreatment is to make the cellulose accessible to the enzymes by destructuring the lignocellulosic matrix. During the pretreatment by vapor explosion, preferably the hemicellulose is attacked, which is found in large part in the liquid phase exiting from the pretreatment.

Typically, the operating conditions for the pretreatment by vapor explosion are as follows:

T=150 to 250° C.
P=10 to 50 bar
Period of pressurization=several seconds to several minutes It should be noted that additional stages following the pretreatment stage, for example setting the pH or liquefaction, can be carried out so as to facilitate the implementation and the effectiveness of the stages of enzymatic hydrolysis and ethylic fermentation.

The pretreated substrate preferably contains between 5% by weight and 80% by weight of MS, more preferably between 15% by weight and 60% by weight of MS, and even more preferably between 20% by weight and 55% by weight of MS.

The pretreated substrate is sent directly via the lines 5 and 7 into a conversion unit 8 that carries out the transformation of cellulose into alcohols. This conversion unit comprises at least one enzymatic hydrolysis unit 9 and a fermentation unit 10 that may be, for example, of one of the following types: butylic, isobutylic, ethylic or other alcohols. In FIG. 1, the enzymatic hydrolysis and fermentation units are shown in a separate manner from one another; however, it is possible within the framework of this embodiment to have a single reactor in which hydrolysis and fermentation (SSF Process) are carried out according to the selected fermentation.

The conditions of enzymatic hydrolysis, primarily the level of dry material of the mixture that is to be hydrolyzed and the amount of enzymes used, are selected in such a way that a solubilization of the cellulose of between 20% and 99%, and in a preferred manner between 30% and 95%, is achieved. The water that is necessary for achieving the targeted MS level is added via a pipe (not shown). The desired level of MS is generally between 5% by weight and 45% by weight and preferably between 8% by weight and 40% by weight.

According to the invention, the enzymatic hydrolysis is preferably carried out at a pH of between 4 and 5.5 and at a temperature of between 40° C. and 60° C.

The necessary additives, for example the cellulolytic enzymes and/or the hemicellulolytic enzymes and the microorganisms of fermentation (if the conversion reaction is in a single stage), of water, of nutrients, of chemical reagents, such as, for example, soda and/or ammonia and/or potash, are introduced via a pipe (not shown) that is dedicated to this purpose.

As mentioned above, it is possible to carry out the enzymatic hydrolysis and the ethylic fermentation (of hexoses or hexoses and pentoses) in one and the same operation referred to by the term SSF. This operation is preferably carried out at a temperature of between 30° C. and 45° C. and at a pH of between 4 and 7.

In an optional manner and according to the fermentation microorganism(s) that is/are used, all or part of the pentoses can also be fermented, as may be the case when a bacterium of the genus *Clostridium* is used for carrying out a butylic fermentation.

A fermented must, comprising a solid residue and a wine, which is brought into a unit 12 for extraction/purification of alcohols contained in the wine, is extracted via the pipe 11 from the conversion unit 8. This extraction/purification stage in general comprises at least one distillation stage.

From the extraction/purification unit 12, there is recovered at least:
An effluent that contains alcohols via the line 13;
A pulp, drawn off via the line 14, containing an insoluble residue that is in part composed of cellulose and hemicellulose that have not been hydrolyzed and lignin mixed with a liquid fraction (or vinasse) that contains unfermented sugars such as pentoses and optionally hexoses.

The pulp is transferred to a solid/liquid separation unit 15 from where a moist cake that comprises cellulose and hemicellulose that have not been hydrolyzed and lignin is recovered via the line 16, and a clarified vinasse that contains unfermented sugars, for example unfermented pentoses (xylose, arabinose), is recovered via the line 17. The moist cake may be either reintroduced into the process or upgraded to produce energy by, for example, methanization or combustion or as an agricultural supplement (spreading).

With reference to FIG. 1, a fraction of the clarified vinasse, between 10% and 90% by weight and preferably between 15% and 60% by weight, is sent via the pipe 17 to a reactor 19 for additional fermentation.

According to an alternative embodiment and as shown in FIG. 1, the pretreated substrate is extracted via the pipe 5 and sent to a solid/liquid separation unit 6 (shown in dotted form). The solid/liquid separation unit 6 makes it possible to separate via the line 18 a liquid flow that contains solubilized sugars during the pretreatment and a moist pulp that is sent via the pipe 7 into the conversion unit 8. The solubilized sugars are obtained essentially from hemicellulose and comprise pentoses and optionally hexoses according to the type of treated biomass. The liquid that contains solubilized sugars is also sent via the line 18 into the additional fermentation reactor 19.

The reactor 19 is a reactor for fermentation of pentoses and optionally residual hexoses into alcohols. The microorganisms that are used for the fermentation of the residual pentoses and hexoses may be bacteria, yeasts or fungi. In a preferred manner, the reactor 19 carries out a fermentation of the ethylic or butylic type so as to produce an ABE (acetone, butanol, ethanol) wine or an IBE (isopropanol, butanol, ethanol) wine or an ABEI (acetone, butanol, ethanol, isopropanol) wine. As mentioned above, the microorganisms may be selected from among those of the genus Clostridium, bacteria that ferment the pentoses very well. Another preferred possibility consists in carrying out an isobutylic fermentation with the microorganisms cited above.

All or part of the wine produced by the fermentation reactor 19 is then transferred, via the pipe 20, into a treatment unit 21.

The treatment unit 21 can comprise, for example, a device for evaporation or heating completed by a unit for separation of materials in suspension (e.g., by centrifuging and/or by decanting and/or by membrane treatment (ultrafiltration, microfiltration)).

The effluent, in vapor or liquid form, obtained from the treatment unit 21 and essentially containing water and alcohols obtained from the fermentation (with a minimum quantity of compounds such as furfural, acetic acid), can be separated into two flows, as indicated in FIG. 1. One of the flows 24 is then sent to the pretreatment reactor 4 and/or to the reactor for preparation of the biomass 2. The other portion of the flow 23 may optionally be recycled in the distillation unit 12.

One advantage of initiating the recycling of the fraction 24 in the pretreatment reactor 4 and/or in the reactor for preparation of the biomass 2 is that this recycling flow makes it possible to replace all or part of the addition of water necessary to these stages.

Typically, the quantity of alcohols recycled in the vapor explosion reactor 4 is adjusted in such a way as to obtain an alcohol content in the reactor 4 of less than 15% by weight, and preferably less than 10% by weight. The acetic acid, the furfural and the other compounds provided by the recycling have concentrations in the reactor 6 that are less than 5% by weight, and even less than 2% by weight.

In a preferred manner, the treatment unit 21 comprises at least one evaporation unit. The evaporation of the flow makes it possible to recycle only the volatile products and, therefore, to avoid recycling the soluble products such as the residual sugars (hexoses and pentoses) that may become degraded in the vapor explosion reactor into furfural, 5-HMF or else into organic acids (formic, levulinic).

The alcohols and optionally the other components mentioned above that are recycled in the pretreatment reactor 4 are recovered after the pressure relief phase in gaseous form with the water vapor via the pipe 27. The gaseous effluent is then transferred to a distillation unit 28 that produces at least two flows: one flow 29 that for the most part contains alcohols and one flow 30 that for the most part comprises water. The flow 29 can be reintroduced into the main extraction/separation unit 12 or sent into a dedicated unit for extraction/separation of alcohols (not shown).

According to an alternative embodiment that is not shown in FIG. 1, the gaseous effluent recovered after pressure relief of the pretreatment reactor 4 is sent directly to the extraction/separation unit 12.

Figure 2:
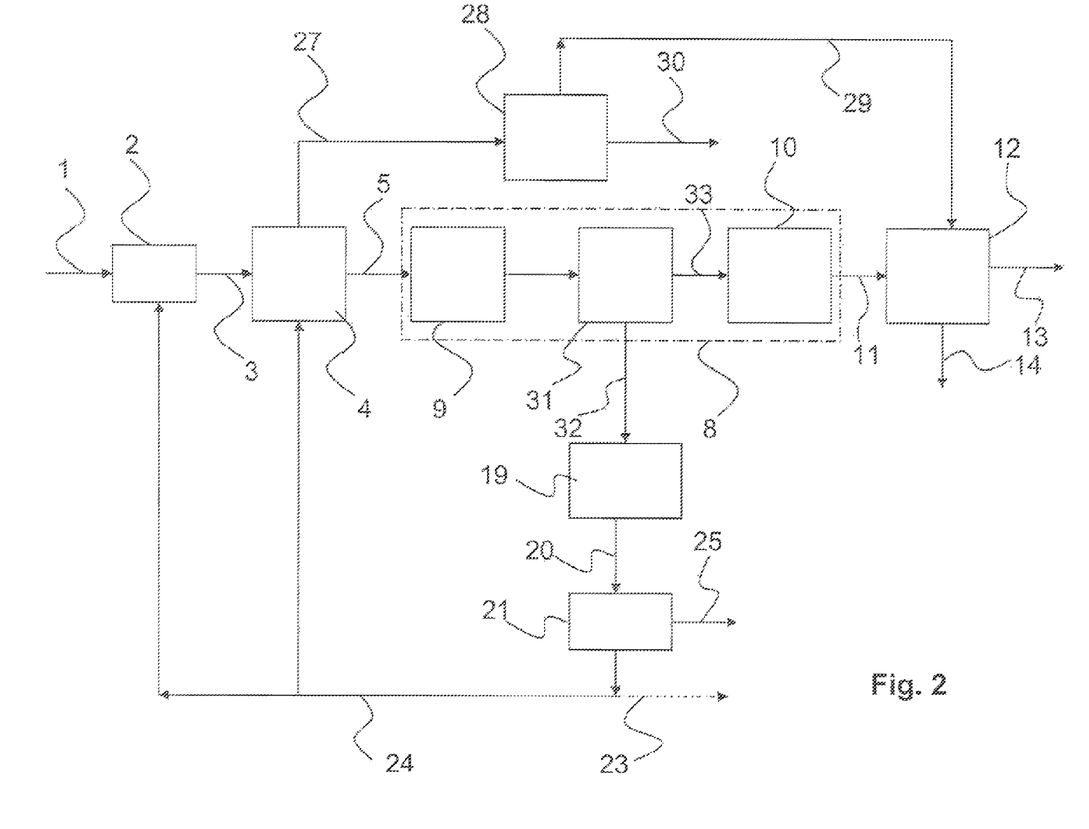
FIG. 2 is a diagrammatic representation of a second embodiment of the process for the production of alcohols according to the invention.

FIG. 2 shows another embodiment of the process according to the invention that differs from the one presented in FIG. 1 by virtue of the fact that:

The conversion unit 8 comprises an enzymatic hydrolysis reactor 9, a fermentation reactor 10 that is separated from the one for enzymatic hydrolysis, and a device 31 for solid/liquid separation placed between said reactors 9 and 10;

The flow that contains alcohols that is recycled is obtained from a pulp produced by solid/liquid separation of the hydrolyzate obtained from the enzymatic hydrolysis and that has then undergone a stage for fermentation of C6 sugars and optionally C5 sugars contained in said pulp.

With reference to FIG. 2, the hydrolyzate obtained from the hydrolysis reactor is sent into the solid/liquid separation device 31 from where there is separated:

A liquid flow 33 that is sent into the reactor 10 for fermentation of alcohol; and A pulp that contains a solid residue that is impregnated with a juice that contains C6 sugars and optionally C5 sugars.

The pulp, by means of the pipe 32, is sent into a reactor 19 for additional fermentation of hexoses and optionally pentoses. For example, the reactor 19 is a fermentation reactor of the ethylic, butylic or isobutylic type.

The fermented must that is obtained from the fermentation reactor 19 that comprises a wine in a mixture with the solid residue is transferred via the pipe 20 into a treatment unit 21 that comprises a solid-liquid separation device completed by means for heating and/or evaporation of the wine that is obtained after solid/liquid separation of the fermented must. All or part of the wine that is heated or in vapor form is recycled in the pretreatment reactor 4 and/or in the reactor for preparation of the biomass 2 via the pipe 24. The solid residue that is extracted from the fermented must is evacuated to the outside of the process via the line 25.

According to an alternative mode of the process according to FIG. 2, the pulp that is extracted from the pipe 32 is subjected to a washing stage and then to solid/liquid separation so as to recover a juice that contains hexoses (and optionally pentoses) and a moist cake. The moist cake is either evacuated to the outside of the process or is recycled in the fermentation reactor 10 while the sugary juice is sent into the fermentation reactor 19 for producing a wine that is then recycled in the pretreatment reactor 4 and/or in the reactor for preparation of the biomass 2, optionally after treatment in a heating or evaporation unit 21.

Figure 3:
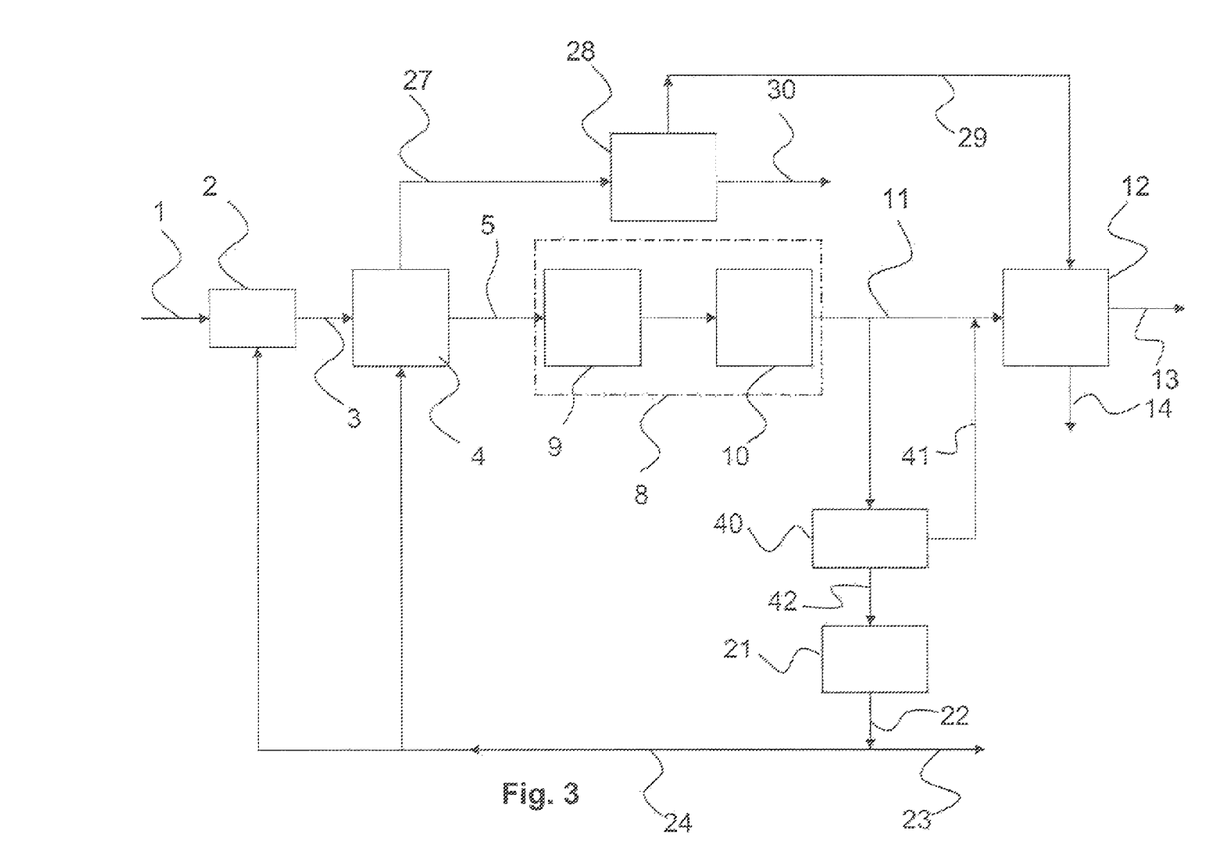
FIG. 3 is a diagrammatic representation of a third embodiment of the process for the production of alcohols according to the invention.

A third embodiment is shown in FIG. 3. This variant is distinguished from the one of FIG. 2 in the following manner:

The solid/liquid separation unit 40 is placed downstream from the conversion unit 8;

The absence of an additional fermentation unit 19.

The fermentation carried out in the reactor 10 is, for example, a fermentation of the butylic or isobutylic type (ABE, IBE, or ABEI).

With reference to FIG. 3, a fraction (or portion) of the fermented must extracted from the fermentation reactor 10 (or from the conversion unit 8 in the case where an SSF process is implemented) is sent into a solid/liquid separation device 40. From the solid/liquid separation device 40, a moist cake is separated via the line 41, and a liquid effluent that contains wine is separated via the line 42. The moist cake is sent into the distillation unit 12 while the wine (e.g., ABE or IBE or ABEI) is treated in a treatment unit 21 (for example, an evaporation unit) before being recycled in the pretreatment reactor 4 and/or in the reactor for preparation of the biomass 2.

According to an alternative embodiment of the process according to FIG. 3, the solid/liquid separation unit 40 is completed by a unit for washing the cake. In this case depicted, the fermented must is separated into a liquid fraction (alcoholic wine) and a solid fraction that contains a moist cake. The liquid fraction is sent to the main extraction/separation unit 12. As for the moist cake (or pulp), it is washed in such a way as to recover washing water that contains more than 70% by weight, preferably more than 85% by weight, of the alcohols contained in the cake. The washing water is heated or evaporated in the treatment unit 21 before being recycled in the pretreatment reactor 4 and/or in the reactor for preparation of the biomass 2. The washed solid residue is recycled to the extraction/separation unit 12 or evacuated to the outside of the process.

Figure 4:
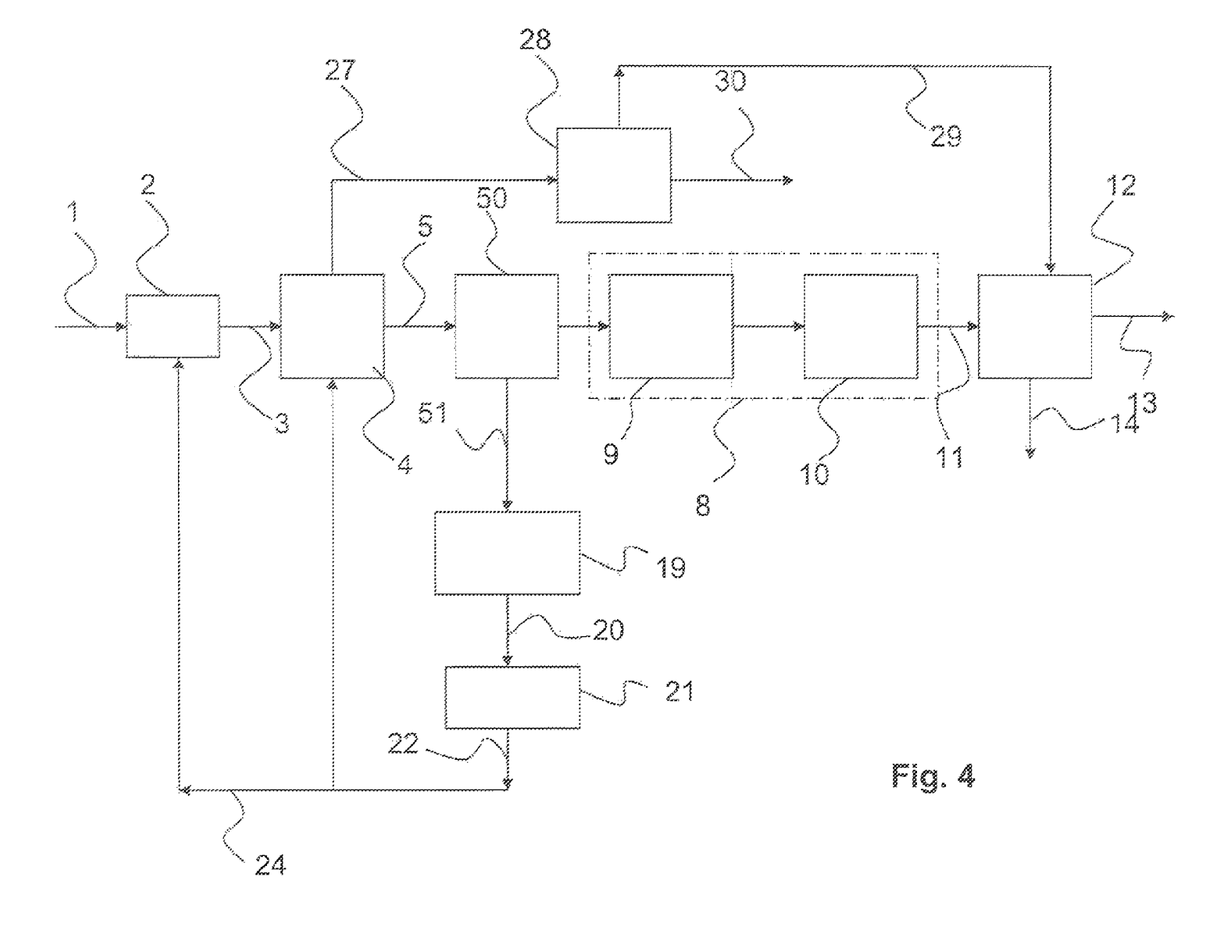
FIG. 4 is a diagrammatic representation of a fourth embodiment of the process for the production of alcohols according to the invention.

FIG. 4 shows another embodiment of the process according to the invention. This embodiment is distinguished from the one of FIG. 1 by the fact that the effluent obtained from the reactor for pretreatment by vapor explosion 4 is treated in a unit 50 that consists of a unit for solid/liquid separation and washing in such a way as to separate a washed moist cake (or pulp) and a liquid effluent that essentially contains pentoses. The pulp is sent into the conversion unit 8 while the liquid effluent is brought using the pipe 51 to the fermentation unit 19. This fermentation stage, as shown in the diagram of FIG. 1, has as its object to carry out, for example, a butylic fermentation (ABE, IBE or a mixture) of the pentoses. The wine that is drawn off from the reactor 19 via the line 20 is sent to the treatment unit 21 so as, for example, to evaporate it. The alcohol vapor is extracted via the line 22 [and] is then recycled in the pretreatment reactor 4 and/or in the reactor for preparation of the biomass 2.

Figure 5:
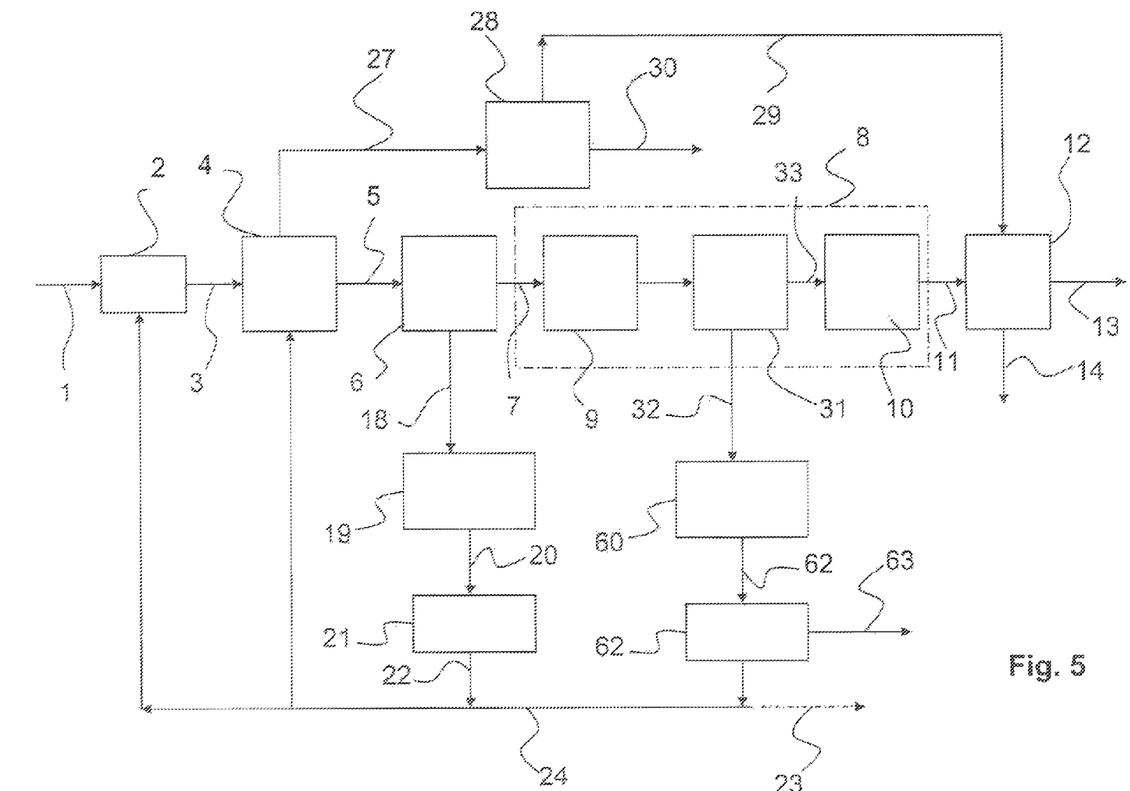
FIG. 5 is a diagrammatic representation of a fifth embodiment of the process for the production of alcohols according to the invention.

FIG. 5 represents another embodiment of the process according to the invention that combines the embodiments of FIGS. 1 and 2. This embodiment implements a first solid/liquid separation stage directly after the vapor explosion stage and a second solid/liquid separation stage between the enzymatic hydrolysis stage and the fermentation stage.

With reference to FIG. 5, the liquid-impregnated pulp drawn off from the vapor pretreatment reactor 4 is sent into a solid/liquid separation device 6 from where a moist cake is extracted via the line 7 and an aqueous effluent that contains essentially pentoses is extracted via the line 18. As in the diagram of FIG. 1, the aqueous effluent is treated in a unit 19 for fermentation of pentoses into alcohols. The alcoholic wine that is obtained exiting from the fermentation unit 19 is, for example, evaporated in the treatment unit 21 before being recycled in the reactor for preparation of the biomass 2 and/or in the vapor explosion pretreatment reactor 4.

With regard to the moist cake that is extracted from the solid/liquid separation device 6, it is sent into the conversion unit 8 that comprises an enzymatic hydrolysis reactor 9, a fermentation reactor 10, and a solid/liquid separation device 31 placed between the hydrolysis reactor 9 and the fermentation reactor 10.

The solid effluent that is impregnated with a juice that essentially comprises hexoses (hydrolyzate) obtained from the enzymatic hydrolysis reactor undergoes a solid/liquid separation stage by means of the device 31 so as to extract, via the line 33, a liquid effluent that essentially contains hexoses and, via the line 32, a pulp that contains a solid residue of hydrolysis impregnated with a juice of hexoses (optionally with pentoses).

The pulp that is impregnated with the juice of hexoses is transferred into a fermentation unit 60 that carries out the conversion of hexoses into alcohols (e.g., ethanol, ABE, IBE). The fermented must obtained from the fermentation unit 60 is then treated in a unit 62 that successively comprises a solid/liquid separation device (optionally completed by washing means) and means for heating/evaporating alcoholic wine that is obtained after solid/liquid separation. As shown in FIG. 5, a solid cake is extracted via the line 63 while all or part of the alcoholic wine is recycled in the reactor for preparation of the biomass 2 and/or in the vapor explosion pretreatment reactor 4.

According to an alternative embodiment of the process described in FIG. 5, the flows 18 and 32 are fermented in the same fermentation reactor.

Figure 6:
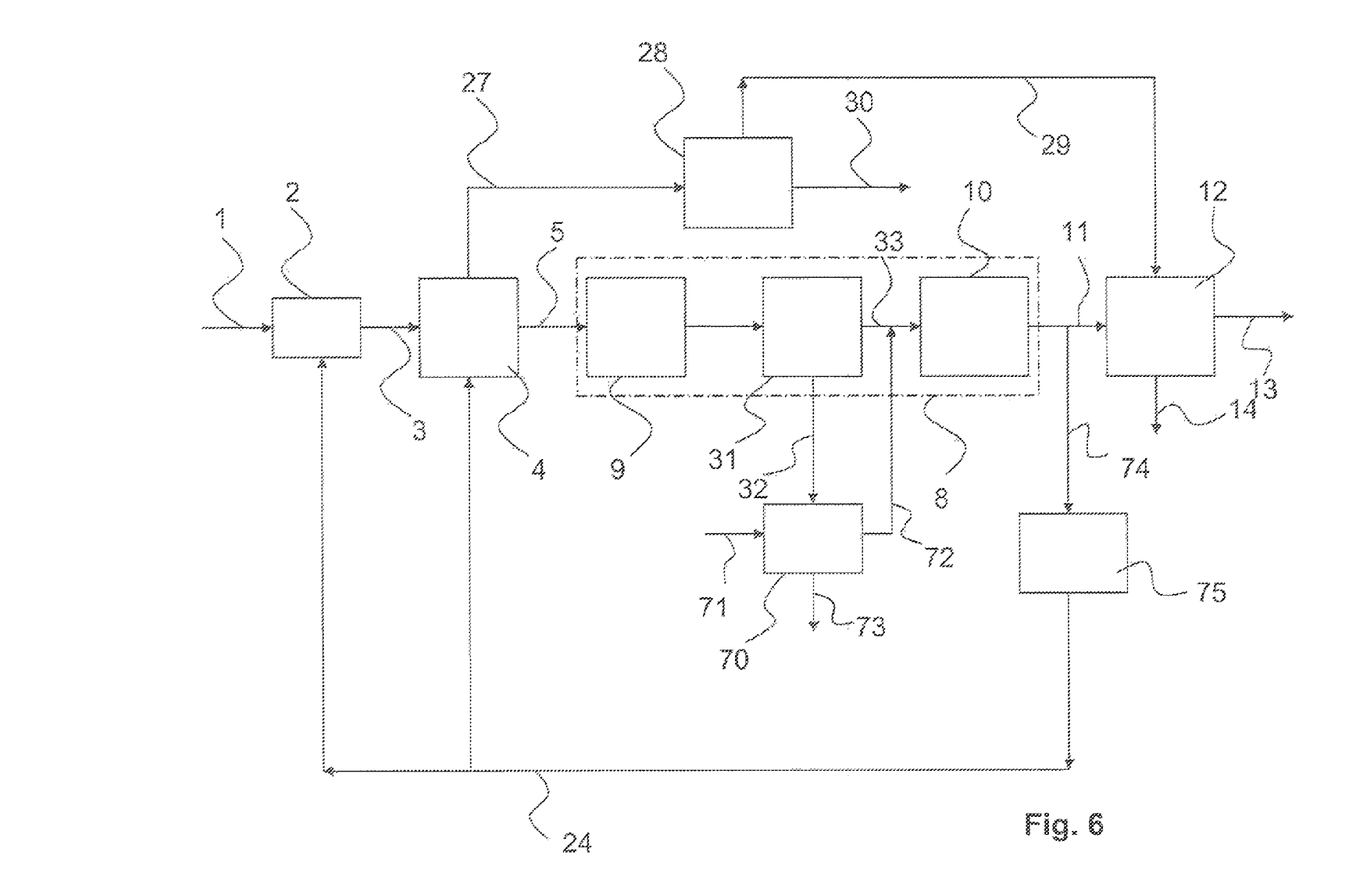
FIG. 6 is a diagrammatic representation of a sixth embodiment of the process for the production of alcohols according to the invention.

FIG. 6 shows a sixth embodiment of the process according to the invention.

With reference to FIG. 6, the hydrolyzate that is obtained from the hydrolysis reactor is sent into the solid/liquid separation unit 31, from where there is separated:

A liquid flow 33 that contains hexoses, which flow is sent into the fermentation reactor 10; and A pulp that contains a solid residue that is impregnated with a juice that contains C6 sugars and optionally C5 sugars.

The pulp that is extracted via the pipe 32 is subjected to a washing stage and then to a solid/liquid separation stage in the unit 70 so as to recover the juice that contains hexoses (and optionally pentoses) via the pipe 72 and a moist cake via the pipe 73. The moist cake is evacuated to the outside of the process while the sugary juice is sent into the reactor 10 for fermentation of sugars into alcohols.

From the fermentation unit 10, a wine is extracted via the pipe 11, of which wine a fraction is extracted via the pipe 74 and is sent into an evaporation unit 75 so as to produce a vapor. The thus generated vapor is then recycled in the pretreatment reactor 4 and/or in the reactor for preparation of the biomass 2. With regard to the other fraction of the wine that is obtained from the fermentation reactor 10, it is treated in the main distillation unit 12 so as to separate the alcohols from the aqueous phase.

EXAMPLES

The examples below illustrate the invention, without limiting its scope.

Example 1

Not in Accordance with the Invention

In this example, a process for producing ethanol, butanol and acetone from wood with the following characteristics is presented:

Feedstock: wood, flow rate 52 tons/hours (dry material base), mean composition:

|  | % (MS Base) |
| --- | --- |
| Cellulose | 40% |
| Hemicellulose (C6) | 7.5% |
| Hemicellulose (C5) | 7.5% |
| Lignin | 33% |
| Others (ashes, extractibles, etc.) | 12% |

Preparation of the feedstock and pretreatment: The wood is ground and then introduced into the vapor explosion reactor continuously; the MS of the solid entering into the explosion is 55%. The pretreatment by vapor explosion is carried out at 210° C. for 5 minutes. The medium is abruptly expanded to a pressure of 1.3 atm. The vapor consumption is 24,305 kWh per hour. 9.3% by mass of the mixture of the explosion reactor is recovered in the vapor phase with pressure relief.

Conversion into Ethanol:

The pretreated substrate is diluted to 10% solids and sent to an enzymatic hydrolysis reactor and then into a reactor for ethylic fermentation of hexoses; the fermentation microorganism is Saccharomyces cerevisae, and the conditions of use of the hydrolysis and the fermentation provide yields of 22.9 g of ethanol per 100 g of MS introduced. The pentoses that are present are not converted by the fermentation microorganism selected in this stage; in contrast, the mannans that are obtained from the hemicellulose are converted. The extracted $CO_2$ is washed for recovering the ethanol fraction entrained in this flow. Thus, the ethanolic titer of the flow sent into distillation is 26.9 g of ethanol/kg of liquid wine.

Separation and Recovery of the Ethanol:

The separation is done by distillation over two columns, the first in the presence of solids. A network of exchangers makes it possible to integrate the separation process thermally. The first column consumes 30,480 kWh per hour in the reboiler. The reboiler of the second column consumes 3,170 kWh per hour. A vinasse/wine heat exchanger makes it possible to recover 27,160 kWh per hour of the vinasse extracted from the first column. Thus, the net consumption of the ethanol recovery stage is 33,650 kWh per hour, or 10.34 MJ/kg of extracted ethanol. The extraction yield is 99%.

ABE Fermentation (Butylic Fermentation) of the Pentoses and Recovery of ABE

After the distillation of the ethanol, the vinasse that contains the pentoses is sent to a solid/liquid separator; the clarified vinasse that represents 84.6% of the initial flow is then sent to a butylic-type fermentation of the pentoses. The microorganism that is used is Clostridium acetobutylicum. The operative conditions of the fermentation have been adjusted to obtain a fermentation yield of 37 g of an ABE mixture per 100 g of xylose, in a respective proportion of 31.2% by weight of acetone, 62.5% by weight of butanol, and 6.3% by weight of ethanol. The separation is carried out by distillation over two successive columns: the first column makes it possible to remove a more concentrated mixture of ABE; the second column makes it possible to obtain an acetone and ethanol mixture at the top and butanol at the bottom, whereas a portion is drawn off onto a decanter plate to be recycled in the first column. The cross-section is integrated thermally, and the respective consumptions of the two reboilers are 24,890 kWh per hour and 960 kWh per hour, to which 460 kWh per hour is added for the exchanger upstream from the first column. The specific consumption is 67.6 MJ/kg of the mixed product.

The process makes it possible to produce 94,730 tons of ethanol, 3,370 tons of acetone, and 6,735 tons of butanol annually, and it has a specific mean consumption of 23 MJ/kg of alcohols and solvents that are produced, including 16.3 MJ/kg for the distillations.

Example 2

In Accordance with the Invention

In this example, a process for the production of ethanol, butanol and acetone from wood with the same characteristics as the process of Example 1 and the implementation of the invention according to the embodiment of FIG. 1 are presented.

Conversion into Ethanol:

The pretreated substrate is diluted to 10% solids and sent into an enzymatic hydrolysis reactor, and then into a reactor for ethylic fermentation of the hexoses. The fermentation microorganism is Saccharomyces cerevisiae and the conditions of use of the hydrolysis and the fermentation provide yields of 22.9 g of ethanol per 100 g of MS that is introduced. The pentoses that are present are not converted by the fermentation microorganism selected in this stage; in contrast, the mannans obtained from the hemicellulose are converted. The extracted $CO_2$ is washed for recovering the ethanol fraction that is driven in this flow. Thus, the concentration of ethanol of the flow that is sent into distillation is 26.9 g of ethanol/kg of liquid wine.

Separation and Recovery of the Ethanol:

The separation is done by distillation over two columns, with the first distillation being carried out in the presence of solids. A network of exchangers makes it possible to integrate the separation process thermally. The first column consumes 30,480 kWh per hour in the reboiler. The reboiler of the second column consumes 3,170 kWh per hour. A vinasse/wine heat exchanger makes it possible to recover 27,160 kWh per hour from vinasse extracted from the first column. Thus, the net consumption of the stage for recovery of ethanol is 33,650 kWh per hour, or 10.34 MJ/kg of extracted ethanol. The extraction yield is 99%.

Implementation of the Invention:

After the distillation of the ethanol, the vinasse that contains the pentoses is sent to a solid/liquid separator; the clarified vinasse that represents 84.6% of the initial flow is then sent to a BUTYLIC fermentation of the pentoses. The microorganism that is used is Clostridium acetobutylicum. The operating conditions of the fermenter are regulated in such a way as to obtain a fermentation yield of approximately 37 g of the ABE mixture for 100 g of xylose and to produce a wine that has in respective proportions 31.2% by weight of acetone, 62.5% by weight of butanol, and 6.3% by weight of ethanol.

10% of the wine is separated and recycled with the pretreatment. The remaining 90% is sent to an ABE separation unit, which is carried out by distillation over two successive columns. The first column makes it possible to remove a more concentrated mixture of ABE, and the second column makes it possible to separate an acetone and ethanol mixture at the top of the second column and the butanol at the bottom.

The vapor flow that comes from the pretreatment and that contains ABE is introduced into the first column. The cross-section is integrated thermally, and the respective consumptions of the two reboilers are 17,260 kWh per hour and 1,130 kWh per hour. The specific consumption is 47.2 MJ/kg of mixed product.

The fraction of the butyl wine that is sent to the vapor pretreatment is first evaporated by bringing the butyl wine to 39 bar and then heated up to 390° C., and finally expanded to 38 bar, for separating the vapor phase (more than 99% of the flow) and a liquid flow that contains the residues of the fermentation. The vapor flow is injected into the vapor explosion reactor, in which there is no supplementary addition of vapor. The consumption of energy for evaporating this flow is 28,035 kWh per hour, after a preheating at 90° C. by exchange with the condenser of the first column for separation from the ABE.

9.3% by mass of the mixture from the vapor explosion reactor is recovered in the vapor phase with pressure relief. Since ethanol and acetone are more volatile than water, the vapor flow becomes enriched with ethanol and acetone. Furthermore, the butanol forms an azeotrope with water whose boiling point is less than that of water in such a way that the vapor phase mixture is therefore also enriched with butanol. Thus, 84% of the products injected with vapor are recovered in the vapor phase exiting from the pretreatment. This vapor flow is then injected into the first distillation column of the ABE mixture. The remainder of the products remains in the liquid phase; the very low concentrations of said products do not have an impact on the stages downstream from hydrolysis and the main ethylic fermentation.

The process makes it possible to produce 94,800 tons of ethanol, 3,300 tons of acetone, and 6,735 tons of butanol annually and with a mean specific consumption of 22 MJ/kg of alcohol and solvents that are produced, including 14.3 MJ/kg for the distillations. This represents an increase in energy of 13% in the distillation section and 5% over the entire process.

Example 3

Not in Accordance with the Invention

In this example, a process for producing isobutanol from straw with the following characteristics is presented:
Feedstock: straw, flow rate 81 tons/hour (dry material base), mean composition:

|  | % (MS Base) |
| --- | --- |
| Cellulose | 38.52% |
| Hemicellulose (C5) | 25.19% |
| Lignin | 22.22% |
| Others (ashes, extractibles, etc.) | 14.07% |

Preparation of feedstock and pretreatment: the straw is ground, the MS regulated at 45% per addition of water, and then the mixture is introduced continuously into the vapor explosion reactor. The pretreatment by vapor explosion is carried out at 200° C. for 3 minutes. The medium is abruptly expanded to a pressure of 1.3 atm. The consumption of vapor is 46,325 kWh per hour. 25% by mass of the mixture from the explosion reactor is recovered in vapor phase with pressure relief.
Enzymatic hydrolysis: Exiting from the pretreatment, 726 tons/hour of water is added to the solid, and then the mixture is sent into enzymatic hydrolysis, where 95% of the cellulose is converted into glucose and 80% of the hemicellulose into xylose. Exiting from the enzymatic hydrolysis, the hydrolyzate is sent to a solid/liquid separator.
Solid/Liquid Separation and Washing:

After the enzymatic hydrolysis, the hydrolyzate is separated by a solid/liquid separator into a liquid flow (810 tons/hour) and a solid pulp (96 tons/hour including 62.6 tons/hour of water). The solid pulp is then washed in a system of 3 countercurrent washing stages with a flow rate of water of 147 tons/hour, which makes it possible to recover 94.6% of the monomer sugars of the liquid phase of the pulp in the washing juice.
Conversion into Isobutanol:

The liquid flow and the washing juice are mixed and then introduced into a reactor for fermentation of the hexoses and the pentoses into isobutanol. 90% of the hexoses and 45% of the pentoses are converted into isobutanol, and the flow exiting from the fermentation has a flow rate of 957 tons/hour and a concentration of 17 g/liter of isobutanol.
Separation and Recovery of Isobutanol:

The separation is done by distillation over two columns, with a decanter inserted between the two columns. A network of exchangers makes it possible to integrate the separation process thermally. The first column makes it possible to separate the water/isobutanol azeotrope from the wine at the top of the column, which is next condensed and then cooled to 60° C. and sent into a decanter, in which the liquid/liquid separation is carried out so as to recover a water-rich phase that is sent to the first distillation column and an isobutanol-rich phase that is sent to the second column. The second column makes it possible to recover the purified isobutanol at the bottom and the water/isobutanol azeotrope at the top that is returned to the decanter. The first column consumes 42,125 kWh per hour in the reboiler. The reboiler of the second column consumes 37,110 kWh per hour. A vinasse/wine heat exchanger makes it possible to recover the heat that is equivalent to 62,000 kWh per hour of vinasse extracted from the first column. Thus, the net consumption of the isobutanol recovery stage is 79,235 kWh per hour, or 17.9 MJ/kg of extracted isobutanol. The extraction yield is 99.5%.

The process makes it possible to produce annually 127,750 tons of isobutanol with a specific consumption of 28.3 MJ/kg of isobutanol, including 17.9 MJ/kg for the distillation.

Example 4

In Accordance with the Invention

In this example, a process for the production of isobutanol from straw with the same characteristics as the process of Example 3 and the implementation of the invention according to the embodiment of FIG. 6 are presented.
Preparation of feedstock and pretreatment: The straw is ground, the MS regulated at 45% by addition of water, and then the mixture is introduced into the vapor explosion reactor continuously. The pretreatment by vapor explosion is carried out at 200° C. for 3 minutes. The medium is abruptly expanded to a pressure of 1.3 atm.
Enzymatic hydrolysis: Exiting from the pretreatment, 733 tons/hour of water is added to the solid, and then the mixture is sent into enzymatic hydrolysis where 95% of the cellulose is converted into glucose, and 80% of the hemicellulose is converted into xylose. Exiting from the enzymatic hydrolysis, the hydrolyzate is sent to a solid/liquid separator.

Solid/Liquid Separation and Washing:

After enzymatic hydrolysis, the hydrolyzate is separated by a solid/liquid separator into a liquid flow (813 tons/hour) and a solid pulp (95 tons/hour including 61 tons/hour of water). The solid pulp is then washed in a 3-stage countercurrent washing system with a flow rate of water of 147 tons/hour, which makes it possible to recover 94.5% of the monomer sugars of the liquid phase of the pulp in the washing juice.

Conversion into Isobutanol:

The liquid flow and the washing juice are mixed and then introduced into a reactor for fermentation of hexoses and pentoses into isobutanol. 90% of the hexoses and 45% of the pentoses are converted into isobutanol; the flow exiting from the fermentation has a flow rate of 958 tons/hour and a concentration of 17 g/liter of isobutanol.

Separation and Recovery of Isobutanol:

The separation is done by distillation over two columns, with a decanter inserted between the two columns. A network of exchangers makes it possible to integrate the separation process thermally. The first column makes it possible to separate the water/isobutanol azeotrope from the wine at the top of the column that is next condensed and then cooled to 60° C. and sent into a decanter where the liquid/liquid separation is carried out in such a way as to recover a water-rich phase that is sent to the first distillation column, and an isobutanol-rich phase that is sent to the second column. The second column makes it possible to recover the purified isobutanol at the bottom and the water/isobutanol azeotrope at the top that is returned to the decanter. The first column consumes 27,430 kWh per hour in the reboiler, with the other portion of the heat being provided by the vapor flow obtained from the pretreatment. The reboiler of the second column consumes 37,410 kWh per hour. A vinasse/wine heat exchanger makes it possible to recover 62,000 kWh per hour of the vinasse extracted from the first column. Thus, the net consumption of the stage for recovery of the isobutanol is 64,840 kWh per hour, or 14.6 MJ/kg of extracted isobutanol. The extraction yield is 99.5%.

Implementation of the Invention:

Exiting from the isobutanol fermentation reactor (ISOBUTYLIC fermentation), a portion (6% by weight of the wine extracted from the fermentation reactor) of the butyl wine is used as an internal flow for recycling in the vapor explosion reactor. This fraction is first brought to 39 bar and heated up to 380° C., and then expanded to 38 bar, for separating the vapor phase (more than 99% of the flow) and a liquid flow that contains the residues of the fermentation. The vapor flow is then injected into the vapor explosion reactor in which there is no supplementary addition of vapor. The consumption of energy for evaporating this flow is 45,940 kWh per hour.

27% by weight of the mixture from the explosion reactor is recovered in the vapor phase with pressure relief. During the pressure relief, the vapor phase becomes enriched with isobutanol. Thus, 93% by weight of isobutanol injected into the vapor explosion reactor is recovered in the vapor phase exiting from the pretreatment. This vapor flow is then injected into the first distillation column. The proportion of isobutanol that remains in the liquid phase at the end of the pressure relief is less than 1 g/liter. This small quantity of isobutanol does not have an impact on the stages downstream from the vapor pretreatment, namely the stages of hydrolysis and fermentation of isobutanol.

The process makes it possible to produce 127,750 tons of isobutanol annually and with a specific consumption of 24.9 MJ/kg of isobutanol, including 14.6 MJ/kg for the distillation. This represents an increase in energy of 19% in the distillation section and 12% over the entire process.

The invention claimed is:

1. A process for the production of alcohols that have two or more carbon atoms from biomass that comprises at least the following stages:
    a) pretreating the biomass in a pretreatment reactor by vapor explosion whereby an effluent that contains a pretreated substrate is produced;
    b) enzymatically hydrolyzing the pretreated substrate contained in the effluent obtained from stage a) in the presence of cellulolytic and/or hemicellulolytic enzymes whereby a hydrolyzate that contains solubilized sugars is produced;
    c) alcoholically fermenting the solubilized sugars contained in the hydrolyzate obtained from stage b) into alcohols that have at least two carbon atoms in the presence of an alcohologenic microorganism whereby a fermented effluent is produced;
    d) extracting alcohols that have at least two carbon atoms from the fermented effluent obtained from stage c); and
    e) recycling upstream to the pretreatment reactor at least one aqueous internal flow that comprises at least one alcohol that has n carbon atoms, wherein n is between 2 and 5, inclusive, provided that when the alcohol comprises n=2 carbon atoms, it is in a mixture with at least one other alcohol, whereby a vapor phase effluent that contains alcohols exiting from said pretreatment reactor is recovered.

2. The process of claim 1, wherein the alcohols that have two or more carbon atoms are selected from among the alcohols that have 2, 3, 4 or 5 carbon atoms, by themselves or in a mixture.

3. The process of claim 1, wherein the internal flow comprises alcohols that are selected from among ethanol, propanol, isopropanol, and butanol, alone or in a mixture and provided that when the alcohol is ethanol, it is mixed with at least one alcohol that has 3, 4 or 5 carbon atoms.

4. The process of claim 1, wherein:
    effecting a solid/liquid separation of at least a portion of a vinasse that is produced in stage d) whereby a liquid fraction that contains pentoses is recovered, and
    fermenting the pentoses of the liquid fraction whereby said internal flow that comprises alcohols is produced.

5. The process of claim 1, wherein:
    effecting a solid/liquid separation of at least a portion of the effluent that is obtained from stage a) whereby a liquid fraction that contains solubilized sugars is recovered, and
    fermenting the sugars of the liquid fraction whereby said internal flow that comprises alcohols is produced.

6. The process of claim 1, wherein:
    effecting a solid/liquid separation of at least a portion of the effluent that is obtained in stage a) whereby a pulp is recovered;
    washing said pulp whereby a liquid fraction that contains solubilized sugars is recovered;
    fermenting the solubilized sugars contained in the liquid fraction whereby said internal flow that comprises alcohols is produced.

7. The process of claim 1, wherein the internal flow is obtained from at least a portion of the fermented effluent that is produced in stage c).

8. The process of claim 7, wherein the internal flow is a liquid fraction that is obtained after solid/liquid separation of at least a portion of the fermented effluent that is produced in stage c).

9. The process of claim 7, wherein the internal flow is a liquid fraction that is obtained after the washing of a cake that is obtained from a solid/liquid separation of at least a portion of the fermented effluent obtained in stage c).

10. The process of claim 1, wherein:
effecting a solid/liquid separation of at least a portion of the hydrolyzate that is obtained in stage b) whereby a pulp that contains hexoses and optionally pentoses is recovered;
fermenting the hexoses and optionally the pentoses that are contained in the pulp whereby said internal flow that comprises alcohols is produced.

11. The process of claim 1, wherein:
effecting a solid/liquid separation of at least a portion of the hydrolyzate that is obtained in stage b) whereby a liquid fraction that contains hexoses and optionally pentoses is recovered;
fermenting the hexoses and optionally the pentoses that are contained in the liquid fraction whereby said internal flow that comprises alcohols is produced.

12. The process of claim 1, wherein stages b) and c) are carried out in the same reactor.

13. The process of claim 1, wherein the internal flow that comprises alcohols is evaporated before the recycling stage e).

14. The process of claim 1, wherein the cellulolytic and/or hemicellulolytic enzymes are produced by a microorganism that belongs to the genera *Trichoderma, Aspergillus, Penicillium* or *Schizophyllum*, or an anaerobic bacterium that belongs to the genus *Clostridium*.

15. The process of claim 1, wherein stage c) is carried out in the presence of a microorganism that is selected from among the genera *Clostridium* and *Escherichia coli*.

* * * * *